United States Patent [19]

Nair et al.

[11] 4,098,995

[45] Jul. 4, 1978

[54] POLYGALACTOSIDO-SUCROSE POLY(H-)SULFATE SALTS

[75] Inventors: Vijay Gopalan Nair, Nanuet, N.Y.; Joseph Peter Joseph, Cliffside Park, N.J.; Seymour Bernstein, New City, N.Y.

[73] Assignee: American Cyanamid Company, Stamford, Conn.

[21] Appl. No.: 704,585

[22] Filed: Jul. 12, 1976

[51] Int. Cl.$^2$ ............................................. C07H 13/12
[52] U.S. Cl. .................................... 536/54; 424/180; 536/115; 536/118

[58] Field of Search ........................... 536/118, 115, 54

[56] References Cited

U.S. PATENT DOCUMENTS

| 3,017,407 | 1/1962 | Petracek et al. | 536/118 |
| 3,413,284 | 11/1968 | Grotsch et al. | 536/118 |

*Primary Examiner*—Johnnie R. Brown
*Attorney, Agent, or Firm*—Jack W. Richards

[57] ABSTRACT

Polygalactosido-sucrose Poly(H-)sulfate and salts thereof useful as complement inhibitors.

13 Claims, No Drawings

POLYGALACTOSIDO-SUCROSE POLY(H-)SULFATE SALTS

BACKGROUND OF THE INVENTION

The present invention resides in the concept of certain polygalactosido-sucrose poly(H-)sulfates and salts thereof as novel compounds and their use as inhibitors of the complement system of warm-blooded animals.

Galactosidosucroses such as raffinose, stachyose, verbascose and ajugose are well-known. Moreover, stachyose mono- and trisulfates are known, however, no utility has been disclosed for such sulfates, *J. Pharm. Soc. Japan,* 87: 1052–1056 (1967). Stachyose trisulfate, prepared according to the above Japanese publication, has been tested for complement activity using the tests disclosed herein and found lacking in complement inhibiting activity. Certain sulfated polysaccharides have been reported as having complement inhibiting activity, for example, heparin, *J. Infect. Dis.,* 44: 250–253 (1929); carrageenin, *Immunology,* 8: 291 (1965); and pentosan polysulfo ester, *Chemical Abstracts,* 75: 33179s (1971). However, no art is known which discloses anticomplementary activity for the galacosidosucrose polysulfate salts of the present invention.

The term "complement" refers to a complex group of proteins in body fluids that, working together with antibodies or other factors, play an important role as mediators of immune, allergic, immunochemical and/or immunopathological reactions. The reactions in which complement participates takes place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1$q$, C1$r$ and C1$s$. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, *Bull. World Health Org.,* 39, 935–938 (1968); *Scientific American,* 229, (No. 5), 54–66 (1973); *Medical World News,* Oct. 11, 1974, pp. 53–58; 64–66; *Harvey Lectures,* 66, 75–104 (1972); *The New England Journal of Medicine,* 287, 489–495; 545–549; 592–596; 642–646 (1972); *The Johns Hopkins Med. J.,* 128, 57–74 (1971); and *Federation Proceedings,* 32, 134–137 (1973).

The complement system can be considered to consist of three sub-systems; (1) a recognition unit (C1$q$) which enables it to combine with antibody molecules that have detected a foreign invader; (2) an activation unit (C1$r$, C1$s$, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complements effects membrane damage are discussed in *Annual Review in Biochemistry,* 38, 389 (1969).

It has been reported that the known complement inhibitors epsilon-aminocaproic acid, Suramin Sodium and tranexamic acid have been used with success in the treatment of hereditary angioneurotic edema, a disease state resulting from an inherited deficiency or lack of function of the serum inhibitor of the activated first component of complement (C1 inhibitor), *The New England Journal of Medicine,* 286, 808–812 (1972); *Allergol, Et. Immunopath,* II, 163–168 (1974); and *J. Allergy Clin. Immunol.,* 53, No. 5, 298–302 (1974).

SUMMARY OF THE INVENTION

It has now been discovered that certain polygalactosido-sucrose poly(H-)sulfate salts interact with the complement reaction sequence, thereby inhibiting complement activity in body fluids.

This invention is particularly concerned with all pharmaceutically acceptable polygalactosido-sucrose poly(H-)sulfate salts having complement inhibiting activity of the general formula:

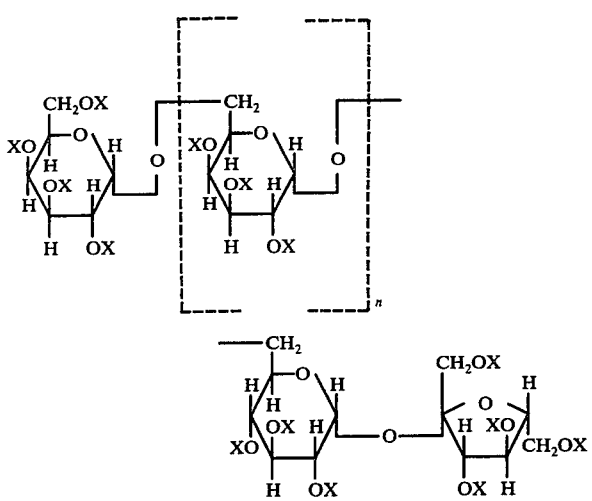

wherein X is —SO$_3$R; R is hydrogen, alkali metal, alkaline earth metal, ammonium and substituted ammonia selected from the group comprising trialkylamines $C_1$-$C_6$); piperidines; pyrazines; cycloalkanolamines ($C_3$-$C_6$); alkanolamines ($C_1$-$C_6$); and $n$ is 0 to 7. For example, when $n=0$, raffinose; $n=1$, stachyose; $n=2$, verbascose and $n=3$, ajugose. The compounds of the present invention are completely sulphated and only completely sulphated compounds are encompassed therein.

Representative polygalactosido-sucrose poly(H-)sulfate salts within the scope of the present invention, include, for example raffinose poly(H-)sulfate triethylamine salt; raffinose poly(H-)sulfate trimethylamine salt; raffinose poly(H-)sulfate sodium salt; stachyose poly(H-)sulfate triethylamine salt; stachyose poly(H-)sulfate trimethylamine salt; stachyose poly(H-)sulfate sodium salt; verbascose poly(H-)sulfate sodium salt; verbascose poly(H-)sulfate trimethylamine salt; verbascose poly(H-)sulfate triethylamine salt; ajugose poly(H-)sulfate sodium salt; ajugose poly(H-)sulfate trimethylamine salt; and ajugose poly(H-)sulfate triethylamine salt.

This invention is also concerned with a method of inhibiting the complement system in a body fluid, such as blood serum, which comprises subjecting body fluid complement to the action of an effective complement inhibiting amount of a polygalactosido-sucrose poly(H-)sulfate salt. The method of use aspect of this invention is further concerned with a method of inhibiting the complement system in a warm-blooded animal which comprises internally administering to said animal an effective complement inhibiting amount of a polygalactoside-sucrose poly(H-)sulfate salt. Body fluid can include blood, plasma, serum, synovial fluid, cerebrospinal fluid, or pathological accumulations of fluid such as pleural effusion, etc.

The polygalactosido-sucrose poly(H-)sulfate salts of the present invention find utility as complement inhibitors in body fluids and as such may be used to ameliorate or prevent those pathological reactions requiring the function of complement and in the therapeutic treatment of warm-blooded animals having immunologic diseases such as rhematoid arthritis, systemic lupus erythematosus, certain kinds of glomerulonephritis, certain kinds of auto-allergic hemolytic anemia, certain kinds of platelet disorders and certain kinds of vasculitis. Polyglactosido-sucrose poly(H-)sulfate salts may also be used in the therapeutic treatment of warm-blooded animals having non-immunologic diseases such as paroxysmal nocturnal hemoglobinurea, hereditary angioneurotic edema (such as Suramin Sodium, etc.) and inflammatory states induced by the action of bacterial or lysosomal enzymes on the appropriate complement components as for example, inflammation following coronary occlusion. They may also be useful in the treatment of transplant rejection and as blood culture and transport mediums.

The compounds of this invention may be prepared by the application or adaptation of known methods, for example, as described in Chemical Reviews, 62: 549–589 (1962); and U.S. Pat. Nos. 3,271,388, 2,923,704, 2,686,779 and 2,697,093, or as described hereinbelow.

Sulfation: Procedure (A)

A mixture of the appropriate polygalactosido-sucrose and the desired triethylamine-sulfur trioxide complex in dry dimethylformamide is heated at a range from 50°–90° C for a period of from 20–24 hours. The solution is cooled and an excess of acetone is added. The solvent is decanted from the separated product and after further purification it is then dissolved in methylene chloride and evaporated in vacuo.

Procedure (B)

An amount of the appropriate polygalactosido-sucrose is added to a stirred solution of the appropriate trimethylamine-sulfur trioxide complex maintained at 65°–75° C. Upon separation of the product stirring is discontinued and heating is continued from 20–24 hours. Upon cooling, the solvent is decanted and further purification with dimethylformamide is performed followed by trituration with absolute ethyl alcohol. The product is collected by filtration and is washed with absolute alcohol followed by anhydrous diethyl ether and then is desiccated.

Salts of Alkali or Alkaline Earth Metals

The appropriate e.g., triethyl- or trimethylammonium salt, of the appropriate polygalactosido-sucrose is dissolved in water and is reacted with a 30% aqueous solution of sodium acetate or calcium acetate. The addition of absolute ethyl alcohol is utilized to ensure complete precipitation of the product which is further purified with absolute ethanol. The precipitation step is repeated and purification with absolute ethanol and anhydrous diethyl ether gives the desired product which is desiccated.

DETAILED DESCRIPTION OF THE INVENTION

The following examples describe in detail the preparation and formulation of representative compounds of the present invention.

EXAMPLE 1

Raffinose Poly(H-)sulfate Triethylamine Salt

A mixture of 750 mg of raffinose pentahydrate and 3.6 g of triethylamine-sulfur trioxide complex is dissolved in 10 ml of dry dimethylformamide with stirring at 50°–55° C for a 24 hour period. The solution is cooled to ambient temperature and a large excess of acetone (about 150 ml) is added to it with the separation of a thick gum. The acetone is decanted off and the product is triturated with acetone several times with decantation of the solvent. The product is finally dissolved in methylene chloride and is then evaporated in vacuo. High vacuum is used to remove the last traces of solvent from the colorless thick gum which is the product of the example.

EXAMPLE 2

Raffinose Poly(H-)sulfate Trimethylamine Salt

A 3.78 g portion of raffinose is added to a stirred solution of 13.76 g of trimethylamine-sulfur trioxide complex in 150 ml of dry dimethylformamide maintained at 75° C. Within a few minutes the sugar is dissolved and the clear solution is heated at 75° C for about 24 hours, a colorless thick gum is separated during this time. The mixture is then cooled and the dimethylformamide is decanted off. The product is triturated with additional dimethylformamide and this solvent is decanted off. The gum is then triturated with absolute ethyl alcohol to form a granular solid which is filtered and is copiously washed with absolute ethanol followed by anhydrous diethyl ether to give a colorless glass as the product of the example.

EXAMPLE 3

Raffinose Poly(H-)sulfate Sodium Salt

A 1.5 g portion of raffinose poly(H-)sulfate triethylamine salt (prepared as in Example 1) is dissolved in 5 ml of distilled water, then 10 ml of a 30% aqueous solution of sodium acetate is added. Absolute ethyl alcohol is then added until precipitation is complete (settles down as a sticky solid). The liquid is decanted off and the gum is redissolved in water and 5 ml of the 30% sodium acetate solution is added followed by the addition of absolute ethyl alcohol. The aqueous ethanol solution is decanted and the gum is then triturated with absoute ethanol to give a colorless granular solid which is filtered and washed several times with absolute ethyl alcohol, followed by anhydrous diethyl ether. The final product of the example is dried in vacuo to give a colorless powder which is stored in a desiccator.

EXAMPLE 4

Stachyose Poly(H-)sulfate Triethylamine Salt

A 666 mg portion of stachyose is dissolved in 10 ml of dry dimethylformamide, then 3.24 g of triethylamine-sulfur trioxide complex is added and the mixture is stirred at about 90° C for about 24 hours. The reaction mixture is cooled and acetone is added resulting in separation of a gummy substance. All the solvent is decanted off and the gum is dissolved in methylene chloride. This solvent is then evaporated in vacuo to give the product of the example as a pale brown glassy material which is desiccated.

EXAMPLE 5

Stachyose Poly(H-)sulfate Trimethylamine Salt

A 55.0 g portion of trimethylamine-sulfur trioxide complex is added to 350 ml of dry dimethylformamide, the mixture is heated with stirring in an oil bath maintained at 75° C. A clear solution results in a few minutes which is cooled slightly, then 15.76 g of stachyose tetrahydrate is added and the resulting mixture is heated in the oil bath at 65° C (a drying tube is affixed to the flask in order to exclude moisture). The sugar is gradually dissolved resulting in a clear solution which, within a few minutes, gradually becomes cloudy and a thick oil separates. It is necessary to discontinue stirring at this point, however, heating is continued for a total of 20 hours. A thick gum is separated and settles in the flask, the dimethylformamide is decanted off and the gum is then triturated with two 50 ml portions of dimethylformamide which is also decanted. The product is then stirred with 400 ml of absolute ethyl alcohol and the gum gradually turns into a colorless crystalline solid. The solid is rapidly filtered and is copiously washed with absolute ethanol and finally three times with anhydrous diethyl ether. The product of the example is then placed in a desiccator.

EXAMPLE 6

Stachyose Poly(H-)sulfate Sodium Salt

A 71.0 g portion of stachyose poly(H-)sulfate trimethylamine salt (prepared as in Example 5) is dissolved in 100 ml of distilled water and 125 ml of a 30% aqueous solution of sodium acetate is added to it. The solution is filtered free of any suspended impurities. The filtrate is allowed to stand for about 10 minutes then about 250 ml of absoluze ethyl alcohol is added to it causing separation of a thick gum. After allowing to stand for a few minutes, additional absolute ethanol is added to ensure complete precipitation of the product. The clear supernatent liquid is decanted off and the gummy product remaining is triturated with absolute ethyl alcohol to gradually yield a colorless granular solid which is filtered and is copiously washed with absolute ethanol followed by anhydrous diethyl ether. The solid obtained is redissolved in about 100 ml of distilled water, then 100 ml of 30% aqueous sodium acetate solution is added to it and the entire operation is repeated. The colorless granular final product of the example is filtered and washed as described above and is then stored in a desiccator.

EXAMPLE 7

Preparation of Compressed Tablet

| Ingredient | mg/Tablet |
| --- | --- |
| *Active Compound | 0.5–500 |
| Dibasic Calcium Phosphate N.F. | qs |
| Starch USP | 40 |
| Modified Starch | 10 |
| Magnesium Stearate USP | 1–5 |

*The polygalactosido-sucrose poly(H—)sulfate salts disclosed herein.

EXAMPLE 8

Preparation of Compressed Tablet — Sustained Action

| Ingredient | mg/Tablet |
| --- | --- |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 9

Preparation of Hard Shell Capsule

| Ingredient | mg/Capsule |
|---|---|
| Active Compound | 0.5–500 |
| Lactose, Spray Dried | qs |
| Magnesium Stearate | 1–10 |

EXAMPLE 10

Preparation of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 11

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 12

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 13

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 14

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 15

Preparation of Intra-Articular Product

| Ingredient | Amount |
|---|---|
| Active Compound | 2–20 mg |
| Na Cl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 16

Preparation of Injectable Depo Suspension

| Ingredient | % W/V |
|---|---|
| Active Compound | 0.05–5 acid(equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

The polygalactosido-sucrose poly(H-)sulfate salts of this invention may be administered internally, e.g., orally, or parenterally, e.g., intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more fo the following identified tests: (i) Test, Code 026 (C1 inhibitor) - This test measures the ability of activated human C1 to destroy fluid phase human C2 in the presence of C4 and appropriate dilutions of the test compound. An active inhibitor protects C2 from C1 and C4; (ii) Test, Code 035 (C3-C9 inhibitor) - This test determines the ability of the late components of human complement (C3-C9) to lyse EAC 142 in the presence of appropriate dilutions of the test compound. An active inhibitor protects EAC 142 from lysis by human C3-C9; (iii) Test, Code 036 (C-Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test — Lethal shock is produced in guinea pigs by an i.v. injection of anti-Forssman antiserum and the harmonic mean death time of treated guinea pigs is compared with that of simultaneous controls; (vi) Complement Level Reduction Test — In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7-8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, code 026, 035, 036, Cap 50, % inhibition and Forssman shock. Table I shows that the compounds of the invention possess complement inhibiting activity.

TABLE I

| | Biological Activities | | | | | | | | | | |
|---|---|---|---|---|---|---|---|---|---|---|---|
| | | | | | | In Vivo Activity (Guinea Pig) Percent Inhibition | | | | | |
| | In Vitro Activity | | | Cap | | Intraperitoneal Time (Hours) | | | Intravenous Time (Hours) | | |
| Compound | 026* | 035* | 036* | 50* | Dose (mg/kg) | 30 | 60 | 120 | 2 | 30 | 120 |
| Raffinose Poly(H—)sulfate Triethylamine Salt | 10** | N | N | 430 | | | | | | | |
| Raffinose Poly(H—)sulfate Sodium Salt | 9 | N | 1 | 330 | | | | | | | |
| Stachyose Poly(H—)sulfate Triethylamine Salt | 9 | N | 2 | 140 | | | | | | | |
| Stachyose Poly(H—)sulfate Trimethylamine Salt | 14 | N | | 148 | | | | | | | |
| Stachyose Poly(H—)sulfate Sodium Salt | 11 | N | 4 | 134 | | | | | | | |
| | 12 | N | | | | | | | | | |
| | 13 | N | 2 | 291 | 200 | −47 | −56 | −65 | −86 | −93 | −17 |
| | 11 | N | 4 | 193 | | | | | | | |

*Code designation for tests employed as referred to herein.
**Activity in wells, a serial dilution assay. Higher well numer indicates higher activity. The serial dilutions are two-fold.
N=inactive

We claim:
1. A compound selected from those of the formula:

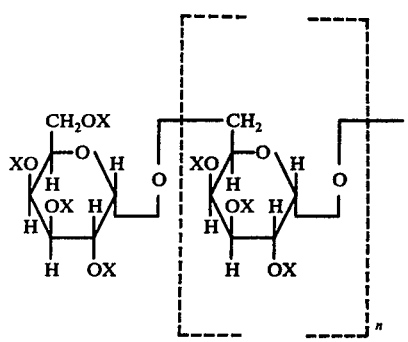

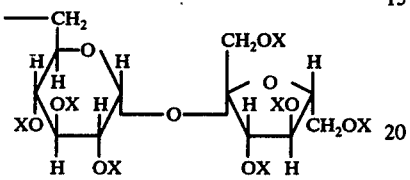

wherein X is —SO$_3$R; R is hydrogen, alkali metal, alkaline earth metal, ammonium and substituted ammonia selected from the group comprising trialkylamine (C$_1$–C$_6$); piperidine, pyrazine; cycloalkanolamine (C$_3$–C$_6$); alkanolamine (C$_1$–C$_6$); and $n$ is 0 to 7.

2. A compound according to claim 1, raffinose poly(H-)sulfate triethylamine salt.

3. A compound according to claim 1, raffinose poly(H-)sulfate trimethylamine salt.

4. A compound according to claim 1, raffinose poly(H-)sulfate sodium salt.

5. A compound according to claim 1, stachyose poly(H-)sulfate triethylamine salt.

6. A compound according to claim 1, stachyose poly(H-)sulfate trimethylamine salt.

7. A compound according to claim 1, stachyose poly(H-)sulfate sodium salt.

8. A compound according to claim 1, verbascose poly(H-)sulfate sodium salt.

9. A compound according to claim 1, verbascose poly(H-)sulfate trimethylamine salt.

10. A compound according to claim 1, verbascose poly(H-)sulfate triethylamine salt.

11. A compound according to claim 1, ajugose poly(H-)sulfate sodium salt.

12. A compound according to claim 1, ajugose poly(H-)sulfate triethylamine salt.

13. A compound according to claim 1, ajugose poly(H-)sulfate trimethylamine salt.

* * * * *